United States Patent
Zarogoulidis et al.

(10) Patent No.: US 11,439,776 B2
(45) Date of Patent: Sep. 13, 2022

(54) DEVICE FOR ADMINISTRATION OF DRY POWDER INHALATION MEDICINE WITH DETACHABLE HEADS FOR ADJUSTING THE RESISTANCE

(71) Applicants: Konstantinos Zarogoulidis, Panorama Thessalonikis (GR); Nikolaos Michailidis, Kalamaria Thessalonikis (GR)

(72) Inventors: Konstantinos Zarogoulidis, Panorama Thessalonikis (GR); Nikolaos Michailidis, Kalamaria Thessalonikis (GR)

( * ) Notice: Subject to any disclaimer, the term of this patent is extended or adjusted under 35 U.S.C. 154(b) by 525 days.

(21) Appl. No.: 16/337,096

(22) PCT Filed: Sep. 28, 2017

(86) PCT No.: PCT/GR2017/000058
§ 371 (c)(1),
(2) Date: Mar. 27, 2019

(87) PCT Pub. No.: WO2018/060748
PCT Pub. Date: Apr. 5, 2018

(65) Prior Publication Data
US 2020/0030554 A1    Jan. 30, 2020

(30) Foreign Application Priority Data
Sep. 28, 2016  (GR) .............................. 20160100493

(51) Int. Cl.
*A61M 15/00*    (2006.01)
(52) U.S. Cl.
CPC ...... *A61M 15/0065* (2013.01); *A61M 15/003* (2014.02); *A61M 15/0021* (2014.02); *A61M 2205/75* (2013.01)

(58) Field of Classification Search
CPC ........... A61M 15/0021–0065; A61M 2205/75; A61M 2205/125; A61M 15/00; A61M 15/002; A61M 15/0023
(Continued)

(56) References Cited

U.S. PATENT DOCUMENTS 4,739,754 A    4/1988  Shaner
5,394,868 A  * 3/1995  Ambrosio ......... A61M 15/0065
                                                  128/203.15
(Continued)

FOREIGN PATENT DOCUMENTS

EP    1 270 034 A2    1/2003
RU       44510 U1      3/2005
(Continued)

OTHER PUBLICATIONS

Merriam-Webster, Screen definition, accessed Jan. 26, 2022, https://www.merriam-webster.com/dictionary/screen (Year: 2022).*
(Continued)

*Primary Examiner* — Elliot S Ruddie
(74) *Attorney, Agent, or Firm* — Finch & Maloney PLLC; Jay S. Franklin; Michael J. Bujold

(57) ABSTRACT

An inhalation delivery device for dry powder with adjusting resistance through detachable heads, which combines four different detachable heads and uses a single base. The desired resistance and the medicament delivery/allocation to the lungs, are set, offering a practical, low cost solution while, at the same time, a high performance personalized treatment. The detachable head (1) comprises a mouthpiece (2) for the mouth of the patient, a medicament intake orifice (3) sized to fit into the mouth of a patient and a protrusion (4) for a sliding connection between the detachable head (1) and the base (5), via notches (6) carried by the base (5). Each detachable head (1) possesses a corresponding protrusion (4)

(Continued)

which may be fitted onto the base (5). The device comprises typically four different heads (1), covering the entire spectrum of patients accordingly to their inhalation capacity, the medicament type/dose and the targeted point of treatment.

10 Claims, 6 Drawing Sheets

(58) Field of Classification Search
USPC .................................................. 128/203.15
See application file for complete search history.

(56) References Cited

U.S. PATENT DOCUMENTS

| | | | |
|---|---|---|---|
| 6,089,228 A * | 7/2000 | Smith | A61M 15/0051 |
| | | | 128/203.15 |
| 6,182,655 B1 | 2/2001 | Keller et al. | |
| 2005/0172955 A1 | 8/2005 | Sundaram et al. | |
| 2006/0041202 A1 | 2/2006 | Farr et al. | |
| 2010/0000530 A1 | 1/2010 | Jauernig et al. | |
| 2010/0065048 A1 | 3/2010 | Mueller-Walz et al. | |
| 2010/0242960 A1 * | 9/2010 | Zangerle | A61M 15/0026 |
| | | | 128/203.15 |
| 2015/0114392 A1 | 4/2015 | Hrkach | |
| 2015/0283338 A1 * | 10/2015 | Colosio | A61M 15/0028 |
| | | | 128/203.15 |

FOREIGN PATENT DOCUMENTS

| | | |
|---|---|---|
| WO | 02/24268 A1 | 3/2002 |
| WO | 2007/093310 A2 | 8/2007 |
| WO | 2015/006838 A1 | 1/2015 |

OTHER PUBLICATIONS

Russian Search Report issued in corresponding Russian Patent Application No. 2019112846 dated Dec. 21, 2020.
Russian Office Action issued in corresponding Russian Patent Application No. 2019112846 dated Dec. 24, 2020.
Greek Search Report Corresponding to 20160100493 dated Oct. 18, 2017.
International Search Report Corresponding to PCT/GR2017/000058 dated Feb. 7, 2018.
Written Opinion Corresponding to PCT/GR2017/000058 dated Feb. 7, 2018.

* cited by examiner

DEVICE FOR ADMINISTRATION OF DRY POWDER INHALATION MEDICINE WITH DETACHABLE HEADS FOR ADJUSTING THE RESISTANCE

The present invention is about a device for administration of dry powder inhalation medicine with adjustable resistance through detachable heads that combines four different detachable heads and uses only one base to adjust pursued resistance and medicine distribution/allocation to the lungs, offering a low cost practical solution and a high-performance individualized treatment at the same time.

Dry powder inhaler (DPIs) are widely and increasingly used in clinical practice because they represent a substantial advancement in inhalation technology, they are more friendly to the environment and more simple to use, without requiring pressurized promotion mechanism. Medicament delivery and lung inherent deposition from a dry powder inhaler are influenced by: a) the patient's inspiratory effort, b) the inhaler resistance and c) the formulation characteristics. Therefore, the respiratory patient profile (graveness of the underlying respiratory disease) is the main concern when creating an effective device, appropriate for dry powder administration. The main attribute that controls the operational flow rate of a dry powder inhaler is the device resistance (pressure drop). There are high-, medium- and low-resistance devices. Asthma and other respiratory diseases have long been treated by the inhalation of appropriate medicament. For many years, the two most widely used and convenient choices of treatment have been the inhalation of medicament from a medicament solution or suspension in a metered dose pressurized inhaler (MDI), or inhalation of powdered medicament generally admixed with an excipient, from a dry powder inhaler (DPI). The growing concern expressed/communicated by the strong link between depletion of the earth's ozone layer and chlorofluorocarbon emissions, led to eliminating the use of such materials in the form of nebula in bronchodilators through devices under pressure, and interest in DPI systems has been stimulated. Well known (or established) single and multiple dose dry powder devices use either individual pre-measured doses, such as capsules containing medicament which is inserted into the device prior to use or incorporate a bulk powder reservoir from which successive quantities of medicament are transferred to a dispensing chamber. The efficiency of aerosolizing the particles of powder in a DPI is dependent upon the patient's inspiratory effort. The dry powder administered is in the form of particles with loose connection between them as well as with the excipients, and the patient must make an increased respiratory effort, so that the medicament particles segregate and enter air flow and subsequently patient's respiratory system. When a patient has breathing problems, e.g., during an asthmatic attack, or when there is a severe and chronic obstructive disease, or in case of an elderly patient, achieving sufficient inspiratory effort may not be possible, in order for the patient to aerosolize and inhale the required dose of medicament, especially at a time when the patient has the greatest need for medicament. If the patient is unable to provide sufficient inspiratory effort the extent of medicament penetration into the lower airways of the lung will be reduced. Moreover, another problem is that larger agglomerated medicament particles (approximately 10 µm or greater) which result from inefficient aerosolisation are not stably entrained into the patient's air stream and prematurely deposit in the mouth/throat region, which may lead to minor therapeutic treatment for the patient.

The present invention proposes a device for administration of dry powder inhalation medicine with adjustable resistance through detachable heads with different levels of resistance. Combining four different detachable heads and using only one base, DPI's pursued resistance, and therefore, medicine distribution/allocation to the lungs are adjusted, covering the entire spectrum of patients, depending on their inspiratory ability, the medicine type/dose and the target treatment point. In this way, a high-performance individualized treatment is provided. Furthermore, the invention's advantage is that it is a low cost practical solution, due to the simplicity of the device.

FIG. 1 shows the invention, and are distinguished the device's base and indicatively one of the heads being used.

In FIG. 2, device's base is illustrated in different views.

Figure 1:
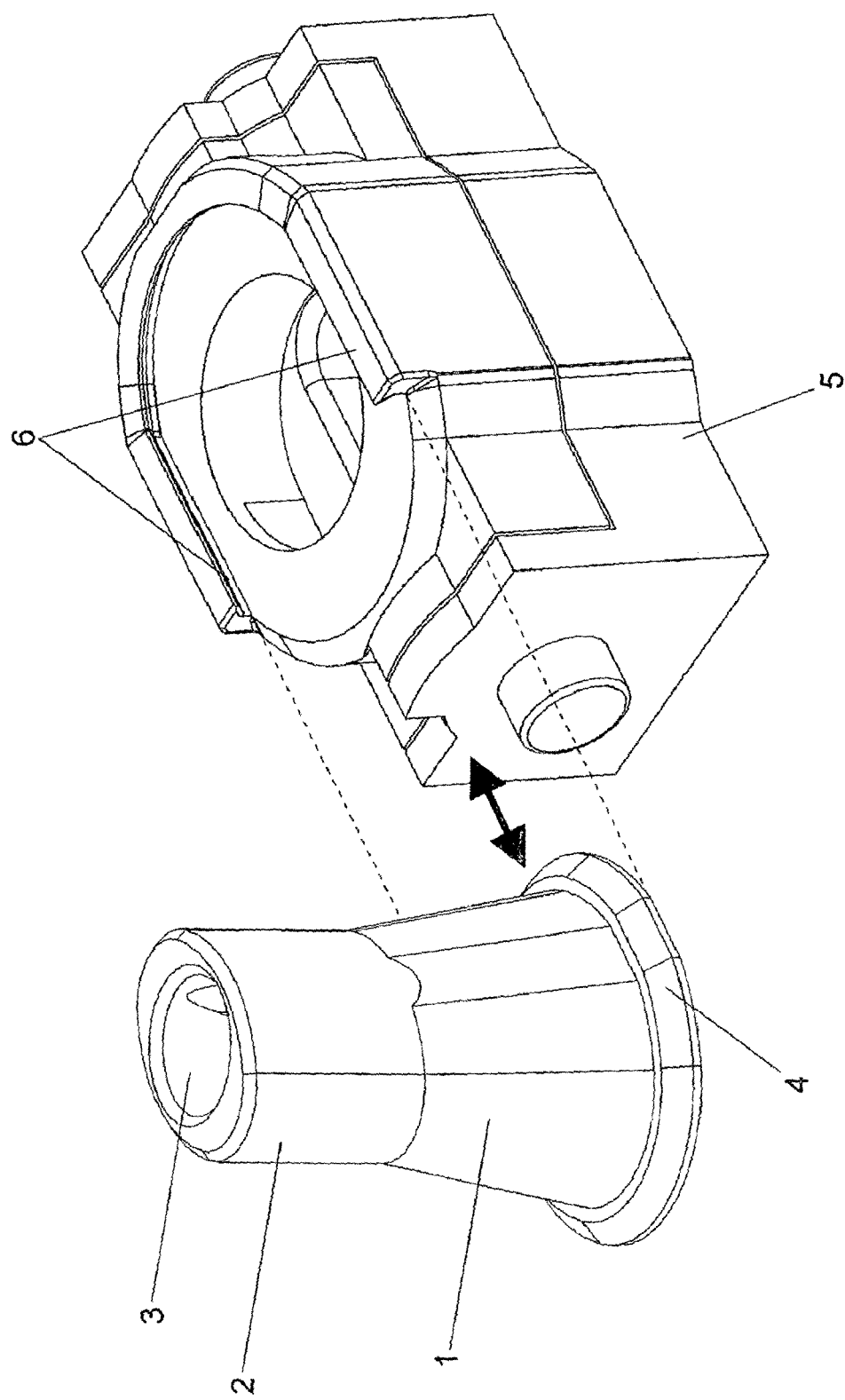

The main invention's elements, presented as the device base and indicatively one of the device heads, are depicted in FIG. 1 and are: head (1) consisting of mouthpiece (2) for patient's mouth application, hole (3) for medicine admission into the mouth and protrusion (4) for sliding connection of the head (1) with the base (5), via notches (6) of the latter. On the base (5), any head (1) with a corresponding protrusion (4) may be adjusted.

Figure 2:
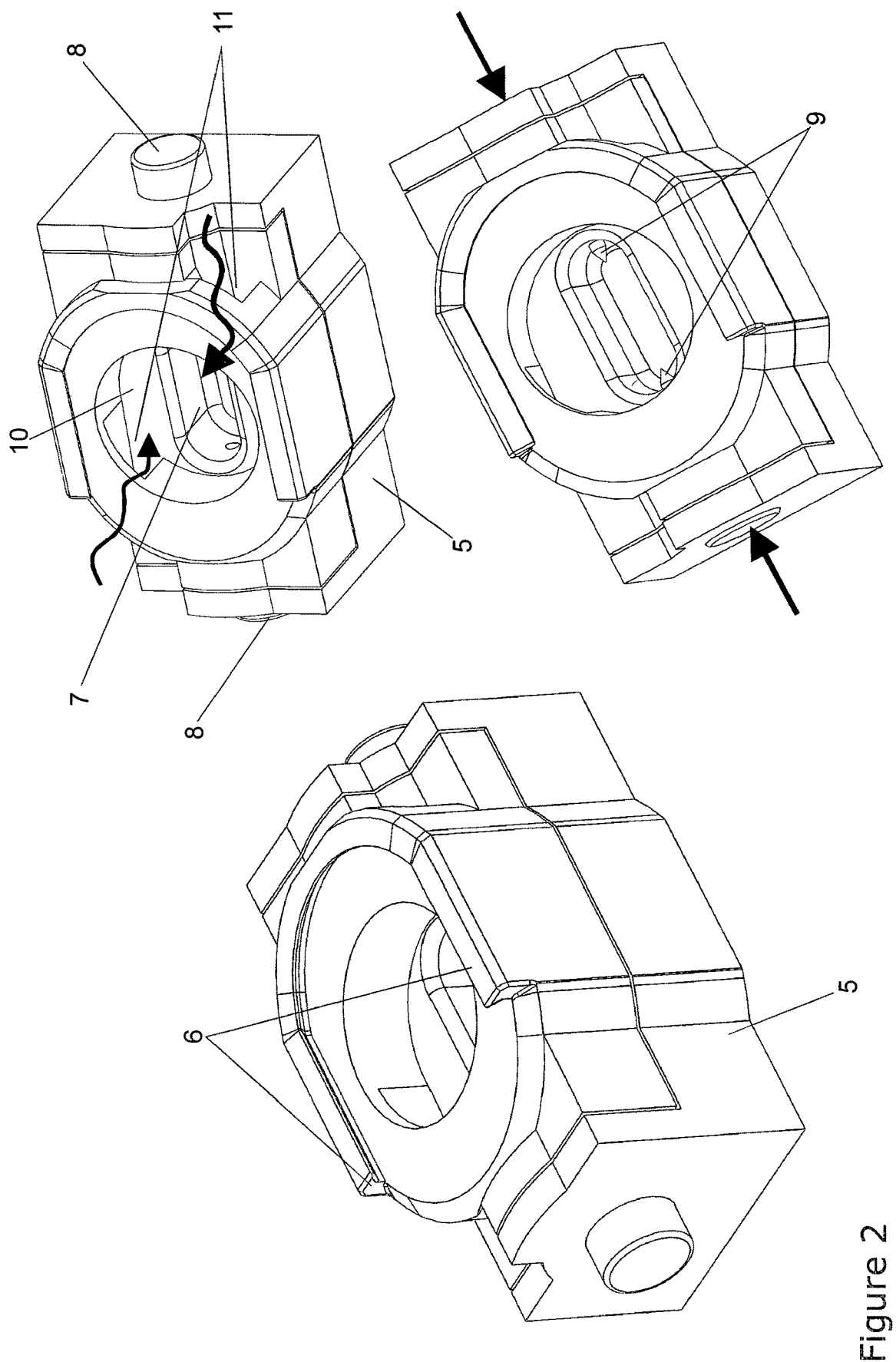

The device base (5), as seen in different views in FIG. 2, is the invention's element where heads (1) are adapted in a sliding way, via protrusion (4) to the notches (6). The base (5) supplies the medicine, as described below. Sequential actions needed for this supply are: First, the capsule containing the medicine is placed in the concavity (7) of base (5). Then, the notches (6) of head (1) slide in the protrusion (4) of base (5) and a chamber (10) is created between base (5) and head (1) that has been selected for use for the patient. When the patient inhales air, the capsule rises from its place in the concavity (7) and revolves (spins/swirls) in the chamber (10). Before inhalation, by pushing the buttons (8), capsule is perforated by spikes (9) that are adjusted to these buttons (8). During inhalation medicine is delivered freely through the holes (by centrifugal forces) that were created into the capsule, as the capsule starts to spin in the chamber (10). Capsule rising from the concavity (7) in the chamber (10) and swirling are achieved through air intakes (11), which, during patient air suction, force regional air import and air swirling in the chamber (10), drifting the capsule together.

Figure 3:
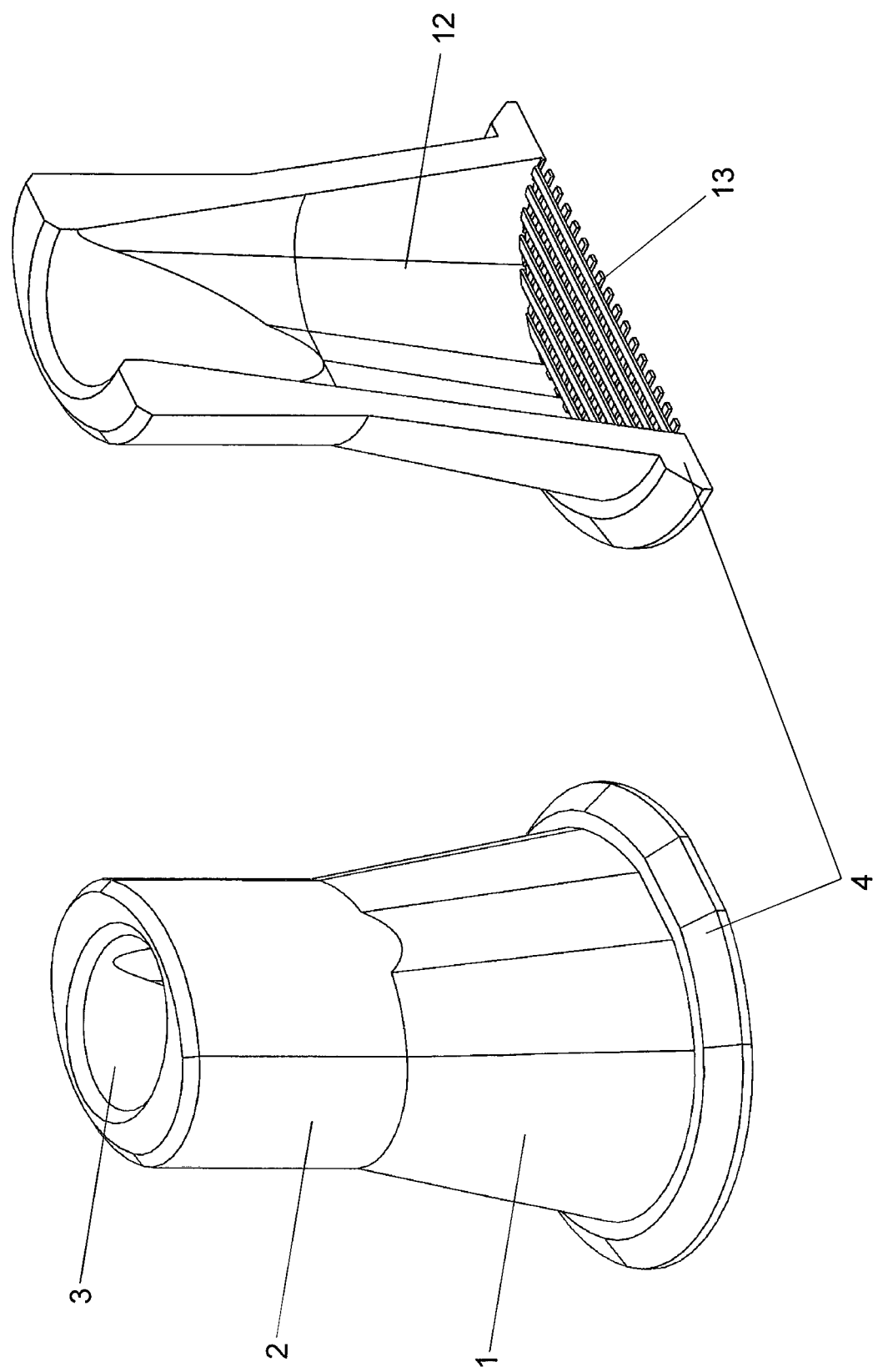
FIG. 3 illustrates a perspective and sectional view of the first device head (Head I).

In FIG. 3 the first head (1) of the device (Head I) is illustrated in a perspective and section view, consisting of the mouthpiece (2) for the patient's mouth application, medicament intake orifice (3) into the mouth and the protrusion (4) for the sliding connection of the head (1) onto the base (5). At the bottom of Head I, there is a mesh (13) that contributes to better medicament aerosolisation and dispersion, while the density and width of its struts achieve more control of the device resistance. Small density or/and small strut width lead to small pressure drop and vice versa. The significant attribute of Head I is its conicity (12) which contributes to the progressive reduction of the diameter of the orifice (3) for the medicament intake into the patient's mouth, leading to smaller pressure drop (low resistance).

Figure 4:
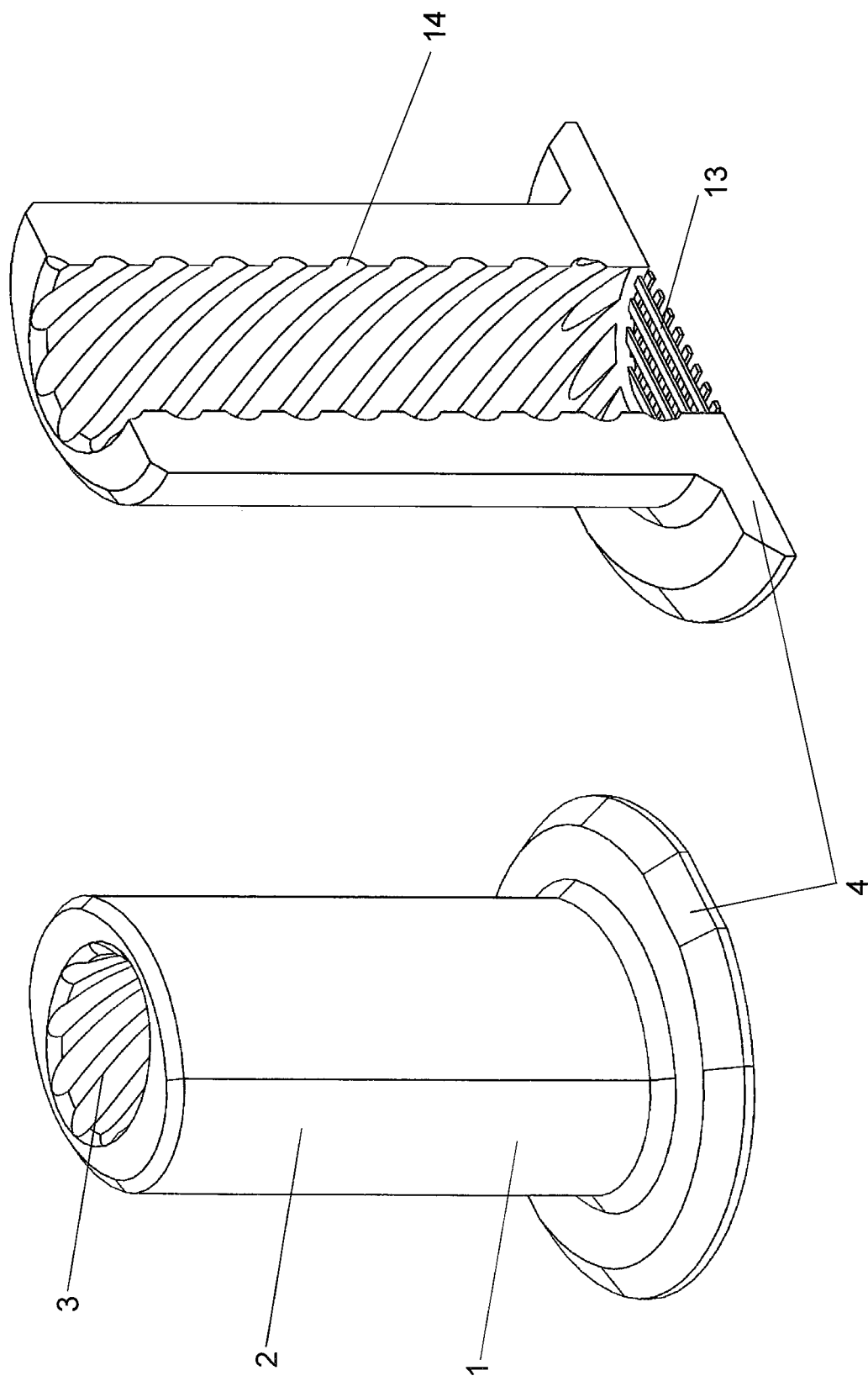
FIG. 4 illustrates a perspective and sectional view of the second device head (Head II).

FIG. 4 illustrates in a perspective and sectional view the second head (1) of the device (Head II), consisting of the mouthpiece (2) for the patient's mouth application, medicament intake orifice (3) for the mouth and protrusion (4) for the sliding connection of the head (1) onto the base (5). At the bottom of Head II there is a mesh (13) that contributes to better medicament aerosolisation and dispersion, while the density and width of its struts achieve more control of the resistance (pressure drop) of the device. Small density or/and small strut width lead to small pressure drop and vice versa. The significant attribute of Head II is that it has elliptical track notches (14) across the entire length of the medicament intake orifice (3) to patient's mouth. The elliptical track notches (14) force the air flow to swirl which entrains the medicament along the airflow, achieving increased medicament penetration into the patient's respiratory system.

Figure 5:
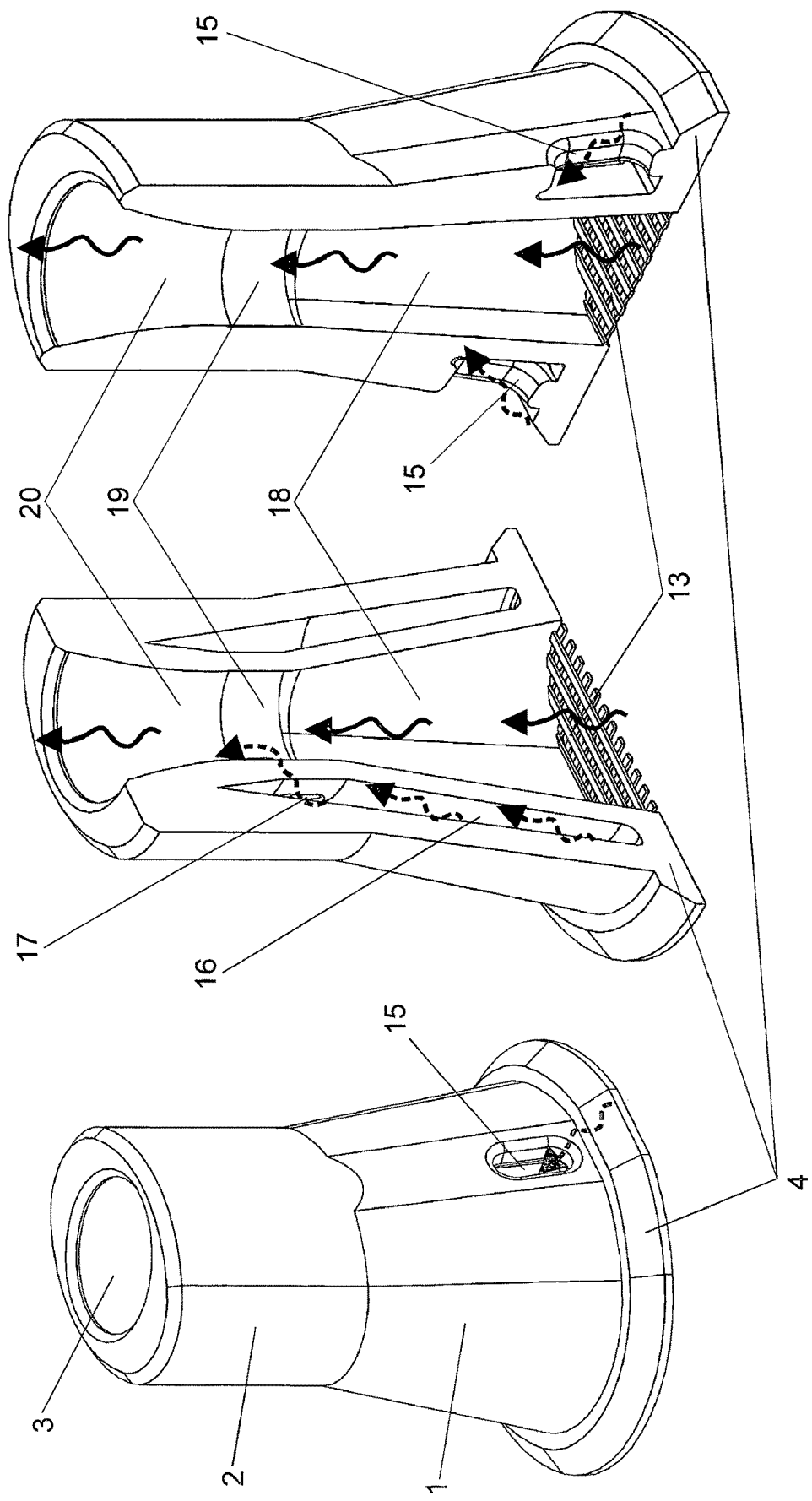
FIG. 5 illustrates a perspective and two different sectional views of the third device head (Head III).

FIG. 5 illustrates in a perspective and two different sectional views the third head of the device (Head III), consisting of the mouthpiece (2) for the patient's mouth application, medicament intake orifice (3) for the mouth and protrusion (4) for the sliding connection of the head (1) onto the base (5). At the bottom of Head III there is a mesh (13) that contributes to better medicament aerosolisation and dispersion, while the density and width of its struts achieve more control of the resistance (pressure drop) of the device. Small density or/and small strut width lead to small pressure drop and vice versa. The significant attribute of Head III is that the medicament intake orifice (3) for the patient's mouth is based on the logic of the Venturi phenomenon. The progressive conical stenosis (18) of the orifice (3) is accompanied by a fixed cross-sectional length segment (19) consisting of circumferential holes (17) and ending with a conical lessening (20). By patient's primary air inhalation (black solid arrow) through the hole (3), the Venturi phenomenon imposes the suction of secondary air (dotted line arrow) through the circumferential holes (17). FIG. 5 illustrates the most complex case where secondary air enters the circumferential holes (17) through bypass/circumferential canals (16) of elliptical orbit fed by the circumpolar holes (15). The diameter and quantity of the circumpolar holes (15) and accordingly of the circumferential holes (17) are affecting the mass and intake speed of secondary air through the intake orifice (3) of the head (1). Large diameter or/and big quantity of circumpolar holes (15) and accordingly of circumferential holes (17) raises the volume of incoming secondary air, although, lowering its speed as well as the speed of primary air and vice versa.

Figure 6:
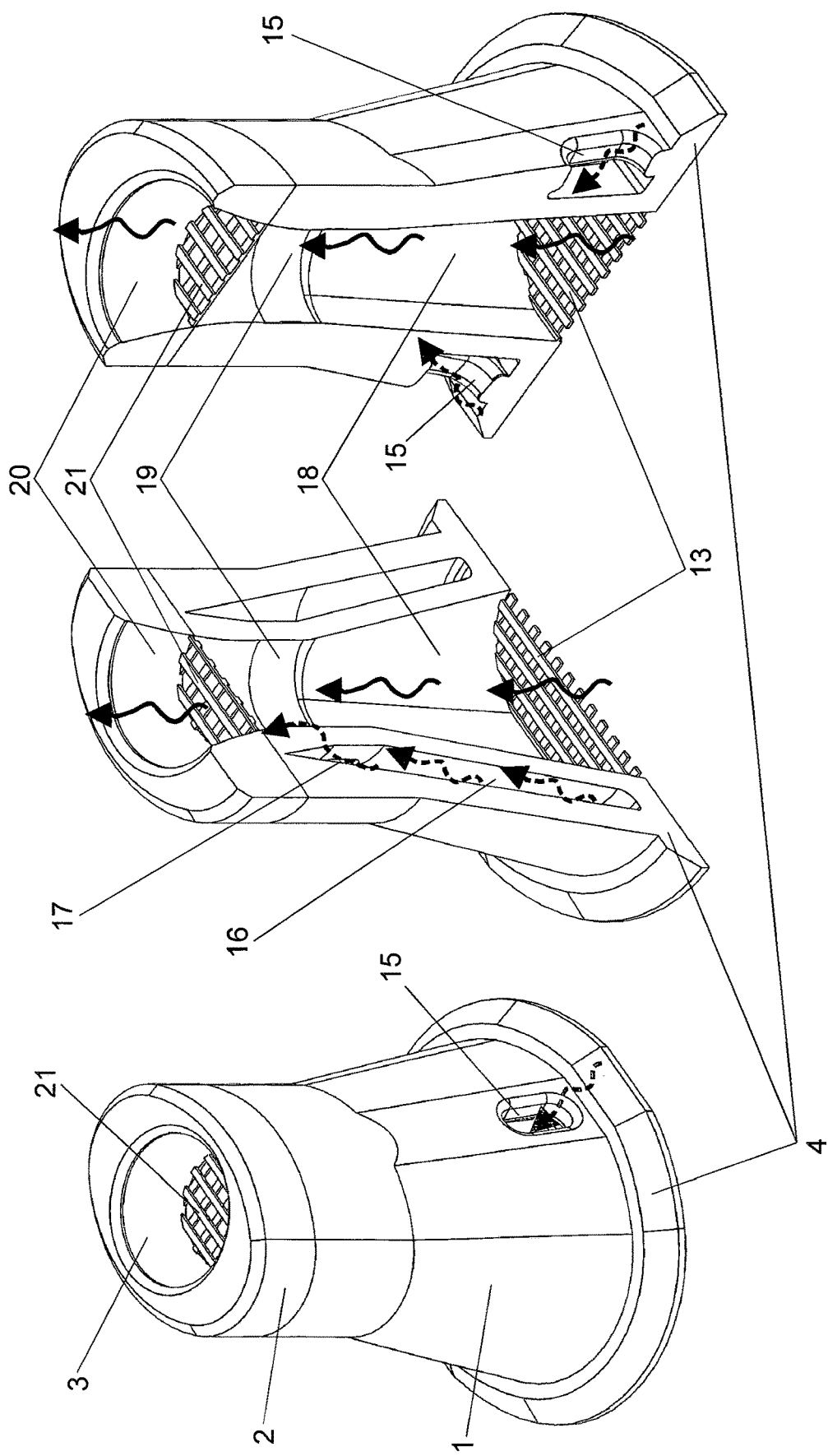
FIG. 6 illustrates a perspective and two different sectional views of the fourth device head (Head IV).

FIG. 6 illustrates in a perspective and two different sectional views the fourth head of the device (Head IV). Head IV is identical with Head III, with the significant attribute of having an extra mesh (21) on the upper part of the mouthpiece (2), permitting to better medicament aerosolisation and dispersion, while the density and width of its struts achieve more control of the resistance (pressure drop) of the device. Small density or/and small strut width lead to small pressure drop and vice versa.

All invention's dimensions and geometric aspects consist variable elements, adjustable to various needs. Furthermore, the device material consists a variable element adjustable to manufacturing capabilities of the manufacturer.

The installation of heads (1) onto the base (5) is customizable, apart from the sliding method above mentioned, but also in a snap or press fashion by adjusting the protrusion (4) of the head (1) and the notches (6) of the base (5).

Παράδειγμα

In the following example, presenting the performance of the four invented heads, stands out the coverage of the whole resistance spectrum (pressure drop) as well as the targeted medicament distribution, by using 10 capsules of TIOTROPIUM BROMIDE 18 mcg/dose for every experiment. The device used, named Andersen Cascade Impactor, is standardized for controlling DPIs. The device is set to operate during the execution of the experiment at an air flow rate of 60 L/min.

The following table presents the inhaling air flows achieved by the four studied heads.

| | Inhaling air flow |
|---|---|
| Head I | >100 L/min at 4 kPa |
| Head II | >84.8 L/min at 4 kPa |
| Head III | >100 L/min at 2.6 kPa |
| Head IV | >62-66 L/min at 4 kPa |

The following tables present medicament concentration at various inhaling partitions, according to the used head.

Head I:

| Distribution in Andersen Cascade Impactor (mcg/dose) | | |
|---|---|---|
| | | Cut-points (μm) |
| Adaptor + induction port | 2.441 | |
| Preseparator | 2.13 | — |
| Stage −1 | 0.351 | 9.0 |
| Stage −0 | 0.465 | 5.8 |
| Stage 1 | 0.893 | 4.7 |
| Stage 2 | 1.13 | 3.3 |
| Stage 3 | 1.491 | 2.1 |
| Stage 4 | 0.506 | 1.1 |
| Stage 5 | 0.105 | 0.7 |
| Stage 6 | 0.038 | 0.4 |
| Filter | 0.018 | — |
| Total dose emitted | 9.568 | |
| Mouthpiece (mcg/dose) | 2.027 | |
| Fine Particle Dose (particles <5 μm) (mcg) | 3.618 | |

Head II:

| Distribution In Andersen Cascade Impactor (mcg/dose) | | |
|---|---|---|
| | | Cut-points (μm) |
| Adaptor + induction port | 1.378 | |
| Preseparator | 2.138 | — |
| Stage −1 | 0.355 | 9.0 |
| Stage −0 | 0.481 | 5.8 |
| Stage 1 | 0.764 | 4.7 |
| Stage 2 | 1.129 | 3.3 |
| Stage 3 | 1.427 | 2.1 |
| Stage 4 | 0.49 | 1.1 |
| Stage 5 | 0.123 | 0.7 |
| Stage 6 | 0.038 | 0.4 |
| Filter | 0.013 | — |
| Total dose emitted | 8.336 | |
| Mouthpiece (mcg/dose) | 1.978 | |
| Fine Particle Dose (particles <5 μm) (mcg) | 3.499 | |

Head III:

| Distributions Andersen Cascade Impactor (mcg/dose) | | |
| --- | --- | --- |
| | | Cut-points (μm) |
| Adaptor + induction port | 2.725 | |
| Preseparator | 2.113 | — |
| Stage −1 | 0.242 | 9.0 |
| Stage −0 | 0.365 | 5.8 |
| Stage 1 | 0.955 | 4.7 |
| Stage 2 | 1.146 | 3.3 |
| Stage 3 | 1.344 | 2.1 |
| Stage 4 | 0.332 | 1.1 |
| Stage 5 | 0.079 | 0.7 |
| Stage 6 | 0.037 | 0.4 |
| Filter | 0.019 | — |
| Total dose emitted | 9.357 | |
| Mouthpiece (mcg/dose) | 1.742 | |
| Fine Particle Dose (particles <5 μm) (mcg) | 3.324 | |

Head IV:

| Distribution In Andersen Cascade Impactor (mcg/dose) | | |
| --- | --- | --- |
| | | Cut-points (μm) |
| Adaptor + induction port | 2.614 | |
| Preseparator | 1.973 | — |
| Stage −1 | 0.26 | 9.0 |
| Stage −0 | 0.322 | 5.8 |
| Stage 1 | 0.697 | 4.7 |
| Stage 2 | 0.914 | 3.3 |
| Stage 3 | 1.391 | 2.1 |
| Stage 4 | 0.49 | 1.1 |
| Stage 5 | 0.107 | 0.7 |
| Stage 6 | 0.036 | 0.4 |
| Filter | 0.026 | — |
| Total dose emitted | 8.83 | |
| Mouthpiece (mcg/dose) | 1.331 | |
| Fine Particle Dose (particles <5 μm) (mcg) | 3.227 | |

The invention claimed is:

1. A device for administration of dry powder inhalation medicine with detachable heads for adjusting a flow resistance, wherein the device comprises:
    a plurality of detachable heads (1) which are interchangeably attachable to a base of the device, each of the plurality of detachable heads comprising;
        a mouthpiece (2) for placement into a mouth of a patient,
        a medicament intake orifice (3) for discharging the dry powder inhalation medicine into the mouth of the patient,
        a protrusion (4) for sliding connection of the detachable head (1) onto the base (5) via corresponding notches (6) carried by the base (5), and
        a mesh (13) is provided, at a bottom of the detachable head (1), that contributes to improved medicament aerosolisation and dispersion,
    the mesh of each of the plurality of detachable heads is configured to facilitate a level of air flow resistance therethrough that is different than a level of air flow resistance through the meshes of the others of the plurality of detachable heads.

2. The device for administration of dry powder inhalation medicine with detachable heads for adjusting the resistance according to claim 1, wherein one of the plurality of detachable heads (1) has a certain conicity (12) contributing to a progressive reduction in a diameter of the orifice (3) to facilitate a relatively high velocity medicament intake into the mouth of the patient.

3. The device for administration of dry powder inhalation medicine with detachable heads for adjusting the resistance according to claim 2, wherein another one of the plurality of detachable heads (1) has elliptical track notches (14) extending across an entire length of the medicament intake orifice (3) to the mouth of the patient which force air flow to swirl and entrain the medicament along the air flow.

4. The device for administration of dry powder inhalation medicine with detachable heads for adjusting the resistance according to claim 2, wherein the medicament intake orifice (3) of another one of the plurality of detachable heads (1) is based on a logic of a venturi phenomenon and has a length portion with progressive conical stenosis (18) and a fixed cross-sectional length segment (19) having circumferential holes (17) and another length portion with a conical lessening (20), such that by primary air inhalation of the patient through the medicament intake orifice (3), the venturi phenomenon facilitates suction of secondary air through the circumferential holes (17); and the secondary air enters the circumferential holes (17) through bypass/circumferential canals (16) of elliptical orbit fed by circumpolar holes (15).

5. The device for administration of dry powder inhalation medicine with detachable heads for adjusting the resistance according to claim 2, wherein another one of the plurality of the detachable heads (1) has an extra mesh (21), provided on an upper part of the mouthpiece (2), which permits improved medicament aerosolisation and dispersion.

6. The device for administration of dry powder inhalation medicine with detachable heads for adjusting the resistance according to claim 1, wherein the plurality of detachable heads comprise dimensions and geometric aspects that are variable for achieving different desired inhalation resistances.

7. The device for administration of dry powder inhalation medicine with detachable heads for adjusting the resistance according to claim 1, wherein the device is manufactured from a polymeric material.

8. The device for administration of dry powder inhalation medicine with detachable heads for adjusting the resistance according to claim 1, wherein installation of the plurality of detachable heads (1) onto the base (5) is achieved apart from a sliding method, but also in a snap fashion by adjusting the protrusions (4) of the plurality of detachable heads (1) and the notches (6) of the base (5).

9. The device for administration of dry powder inhalation medicine with detachable heads for adjusting the resistance according to claim 1, wherein installation of the plurality of detachable heads (1) onto the base (5) is achieved apart from a sliding method but also by a press fashion by adjusting the protrusions (4) of the plurality of detachable heads (1) and the notches (6) of the base (5).

10. The device for administration of dry powder inhalation medicine with detachable heads for adjusting the resistance according to claim 1, wherein the protrusion of each of the plurality of detachable heads extends radially outward and circumferentially about the detachable head, and the notches extend around the base in a shape of a U such that the notches engage with the protrusion on at least opposite sides of the detachable head.

* * * * *